(12) United States Patent
Jarosiewicz et al.

(10) Patent No.: US 9,851,795 B2
(45) Date of Patent: Dec. 26, 2017

(54) CONTEXT-AWARE SELF-CALIBRATION

(71) Applicant: Brown University, Providence, RI (US)

(72) Inventors: Beata Jarosiewicz, Providence, RI (US); Nicolas Masse, Chicago, IL (US); Daniel Bacher, Providence, RI (US); Anish Sarma, Providence, RI (US)

(73) Assignee: Brown University, Providence, RI (US)

( * ) Notice: Subject to any disclaimer, the term of this patent is extended or adjusted under 35 U.S.C. 154(b) by 268 days.

(21) Appl. No.: 14/739,406

(22) Filed: Jun. 15, 2015

(65) Prior Publication Data

US 2015/0370325 A1     Dec. 24, 2015

Related U.S. Application Data (60) Provisional application No. 62/015,344, filed on Jun. 20, 2014.

(51) Int. Cl.
*G06F 3/033*  (2013.01)
*G06F 3/01*   (2006.01)
*G06F 3/038*  (2013.01)

(52) U.S. Cl.
CPC .............. *G06F 3/015* (2013.01); *G06F 3/012* (2013.01); *G06F 3/013* (2013.01); *G06F 3/038* (2013.01)

(58) Field of Classification Search
CPC .......... G06F 3/012; G06F 3/013; G06F 3/015; G06F 3/038; G06F 19/322; G06F 19/3418; A61B 5/0006; A61B 5/04015; A61B 5/0478; A61B 5/048; A61B 5/0484; A61B 5/165; A61B 5/4839; A61B 5/6803; A61B 2560/0431; A61B 5/6816; A61B 5/6831; G06Q 30/0277; B60W 50/08

See application file for complete search history.

(56) References Cited

U.S. PATENT DOCUMENTS

| 7,392,079 B2 | 6/2008 | Donoghue et al. |
| 8,095,210 B2 | 1/2012 | Burdick et al. |
| 2006/0195042 A1 | 8/2006 | Flaherty |

(Continued)

FOREIGN PATENT DOCUMENTS

WO     2003041790 A9    9/2003

OTHER PUBLICATIONS

Beata Jarosiewicz et al, "Advantages of closed-loop calibration in intracortical brain-computer interfaces for people with tetraplegia," Journal of Neural Engineering, 2013, vol. 10; 10 pages.

(Continued)

*Primary Examiner* — Nelson Rosario
(74) *Attorney, Agent, or Firm* — Atesa Legal PLLC (57) ABSTRACT

A method for context-aware self-calibration includes measuring for a plurality of time segments, at least one feature of at least one biosignal or each of at least one channel. Each biosignal is created in response to a user imagining an intended direction for each time segment. An object is moved along an actual decoded direction determined by an output of a decoder configured to correlate for each time segment the at least one feature to the intended direction. The decoder self-calibrates to minimize for each time segment, an error between the actual decoded direction, and the intended direction inferred subsequent to the respective time segment.

20 Claims, 10 Drawing Sheets

(56) References Cited

U.S. PATENT DOCUMENTS

2012/0108998 A1    5/2012  Molnar et al.
2014/0058528 A1    2/2014  Contreras-Vidal et al.
2017/0042439 A1*   2/2017  Yeow .................. A61B 5/0006

OTHER PUBLICATIONS

Leigh R. Hochberg et al, "Reach and grasp by people with tetraplegia using a neurally controlled robotic arm," Nature, May 17, 2012, vol. 485, pp. 372-377; 6 pages.

Alex Kreilinger et al, "Error potential detection during continuous movement of an artificial arm controlled by brain-computer interface," International Federation for Medical & Biological Engineering, 2011; 9 pages.

Gopal Santhanam, "Designing Higher Performance Neural Prosthetic Systems," PHD dissertation, Stanford University, Dept. of Electrical Engineering, Dec. 2006; 167 pages.

PCT International Search Report and Written Opinion for PCT/US2015/035828, dated Sep. 15, 2015; 12 pages.

Ping Zhou et al, "Decoding a New Neural-Machine Interface for Control of Artificial Limbs," J. Neurophysicol, vol. 98, 2007, pp. 2974-2982; 9 pages.

* cited by examiner

FIG. 13
Velocity Bias

FIG. 12
Baseline Bias

FIG. 11
Directional Bias

CONTEXT-AWARE SELF-CALIBRATION

CROSS-REFERENCE TO RELATED APPLICATIONS

This application is a utility application claiming priority to U.S. Provisional Application Ser. No. 62/015,344 filed on Jun. 20, 2014 entitled "CONTEXT-AWARE ADAPTIVE CORRECTION OF OFFSETS," the entirety of which is incorporated by reference herein.

GOVERNMENT RIGHTS IN THE INVENTION

This invention was made with government support under Grant No. A-6779-I awarded by the Department of Veterans Affairs, and N01 HD010018, N01 HD053403, R01 DC009899 and R01 HD063931 awarded by National Institutes of Health. The government has certain rights in the invention.

FIELD OF THE INVENTION

The present invention relates generally to control systems. More specifically, the invention relates to self-calibration in biosignal-controlled systems.

BACKGROUND

Paralysis from spinal cord injuries, degenerative diseases and birth defects can reduce the autonomy and quality of life for those so afflicted. Existing assistive devices for people with severe motor disabilities are inherently limited, relying primarily on residual motor function for their use. For example, the Sip-and-Puff system can control a motorized wheelchair using air pressure by "sipping" (inhaling) or "puffing" (exhaling) into a straw with a pressure sensor.

More recently, brain-computer interfaces (BCIs) are being used to control assistive devices such as computer cursors or robotic arms by decoding neural activity directly from the brain. However, nonstationarities in recorded brain signals can degrade the quality of neural decoding over time. Furthermore, a periodic and frequent interruption to recalibrate the neural decoding algorithm would be both time-consuming and impractical. Signal nonstationarities and very low signal to noise ratios in BCI sensors have thus far limited the ability of disabled persons to have autonomous control of assistive devices, thus significantly diminishing their quality of life.

BRIEF SUMMARY

As will be appreciated, embodiments as disclosed include at least the following. In one embodiment, a method for context-aware self-calibration comprises measuring for a plurality of time segments, at least one feature of at least one biosignal for each of at least one channel. Each biosignal is created in response to a user imagining an intended direction for each time segment. An object is moved along an actual decoded direction determined by an output of a decoder configured to correlate for each time segment the at least one feature to the intended direction. The decoder is calibrated to minimize, for each time segment, an error between the actual decoded direction, and the intended direction inferred subsequent to the respective time segment.

Alternative embodiments of the method for context-aware self-calibration include one of the following features, or any combination thereof. A set of time segments is chosen from the plurality of time segments occurring within a first time of the user imagining the intended direction, prior to at least one of a second time at the end of the actual decoded direction and reaching a proximal distance at the end of the actual decoded direction. The set of time segments includes the at least one channel with a signal to noise ratio (SNR) exceeding an SNR threshold. Calibrating the decoder includes exponentially reducing a contribution of the error for each time segment to calibrating the decoder, in proportion to a temporal proximity of each time segment to a current time segment. Calibrating the decoder includes scaling the error for a recent set of time segments when a range of errors for each time bin exceeds a stability threshold. The plurality of time segments are from one of a plurality of activity blocks, and the user imagines the intended direction towards a target for the respective activity block. The biosignal is created by at least one neuron of the user and the at least one feature includes a threshold crossing rate of the at least one biosignal. The biosignal is responsive to a movement of an eye of the user and includes at least one of an electrical signal and an optical signal. The biosignal is responsive to a movement of a head of the user and includes at least one of an electrical signal and an optical signal.

In another embodiment, a method for autonomous control of assistive devices comprises measuring for a plurality of time segments, at least one feature of at least one neuronal signal for each of a plurality of channels. Each channel is associated with at least one neuron of a user. Each neuronal signal is created by the at least one neuron. Decoding the at least one neuronal signal to move an object along an actual decoded direction determined by an output of the decoder configured to correlate for each time segment, wherein the user imagines an intended direction, the at least one feature to the intended direction. Calibrating the decoder by minimizing an error between the intended actual decoded direction, and the intended direction inferred subsequent to the respective time segment. The at least one feature is normalized during a rest period, wherein the user refrains from imagining the intended direction, by estimating a baseline value of each feature with a recursively-defined exponential estimate, the baseline value of each feature being subtracted from each respective feature for each time segment before being decoded by the decoder. A velocity bias is corrected, wherein the user imagines the intended direction, by determining an exponentially weighted running mean of a decoded velocity for each respective time segment exceeding a speed threshold, and subtracting the exponentially weighted running mean from the decoded velocity.

Alternative embodiments of the method for autonomous control of assistive devices include one of the following features, or any combination thereof. The decoder is a Kalman filter. The feature is a threshold crossing rate of the at least one action potential. The feature is an RMS power of the at least one action potential. The velocity threshold is a predetermined centile of a decoded velocity of a most recent decoder calibration.

In another embodiment, a system for autonomous control of assistive devices comprises a user imagining an intended direction for each of a plurality of time segments by generating at least one biosignal from a part of the user. A biosignal sensor is configured to measure for a plurality of time segments, at least one feature of the at least one biosignal for at least one channel. A device is electrically decoupled from the part of the user. A decoder is configured to correlate for each time segment, the at least one feature to the intended direction, wherein an object is moved along an actual decoded direction determined by an output of the decoder, and the decoder is calibrated by minimizing an error between the actual decoded direction, and the intended direction inferred subsequent to the respective time segment.

Alternative embodiments of the system for autonomous control of assistive devices include one of the following features, or any combination thereof. Each feature is normalized during a rest period, including refraining by the user from imagining the intended direction for at least one time segment, and a baseline value of each feature is estimated with a recursively-defined exponential estimate. The baseline value of each feature is subtracted from each respective feature for each time segment before being decoded by the decoder. A velocity bias is corrected while the user is imagining the intended direction by determining an exponentially weighted running mean of a decoded velocity for each respective time segment exceeding a speed threshold, and subtracting the exponentially weighted running mean from the decoded velocity. The device is a prosthetic limb mechanically coupled to the user. The device is a robotic arm mechanically decoupled from the user. The device is a cursor.

In another embodiment, a method for context-aware self-calibration comprises measuring for a plurality of time segments, at least one feature of at least one biosignal. Each biosignal is created in response to an intended action for each time segment. Performing an actual action is determined by an output of a decoder configured to correlate for each time segment the at least one feature to the intended action. The decoder is calibrated to minimize, for each time segment, an error between the actual action, and the intended action inferred subsequent to the respective time segment.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 4.

DETAILED DESCRIPTION

Embodiments of systems and methods described herein provide for the autonomous control of assistive devices by disabled persons whose neural pathways have been compromised. For example, paralysis following spinal cord injury, brainstem stroke, or amyotrophic lateral sclerosis (ALS) can interrupt the neural pathways between the brain and parts of the body, thereby limiting volitional movements. A neural interface system that can form a bridge across the compromised neural pathway greatly improves the autonomy of these disabled persons, by restoring motor function to functional levels. In some embodiments, an individual controls a prosthetic limb with the bridged neural pathway. In another embodiment, a robotic arm or other remote device is similarly controlled. Embodiments of the present disclosure also include adaptive measurement of biological signals for diagnostic applications, not involving the control of a device.

Autonomous control of assistive devices is enabled through the use of novel context-aware methods. These methods correct offsets in control systems used to control the assistive devices by adaptively calibrating the system with minimal or no need for task interruptions. While embodiments herein are described in the context of people with tetraplegia, the inventive concepts are envisioned to be application to numerous fields, including the provision of a bridged neural pathway for able-bodied individuals. The embodiments described herein are for illustration purposes and are not intended to limit the concepts to the particular field of these embodiments.

In many control systems, data from multiple sensors are used to control a desired system output. Sensors that measure signals such as biopotentials are often contaminated by noise and are susceptible to drift, thus requiring an approach to correct for these errors.

An approach that leverages the context of control system use has been realized to improve offset correction performance even with sensors that contain very low signal to noise ratios and are susceptible to a substantial amount of nonstationarity.

One non-limiting example for adaptive offset correction includes the control of assistive devices through the use of extracted biosignals such as electrical signals recorded from electroencephalography, electrocorticography, electromyography, or multi-electrode recording from the nervous system, or optical signals recorded from head, eye, or finger movements. These systems extract information about a person's movement intention, allowing people with motor disabilities to control computer cursors and other prosthetic or assistive devices with minimal or no overt movement.

Figure 1:
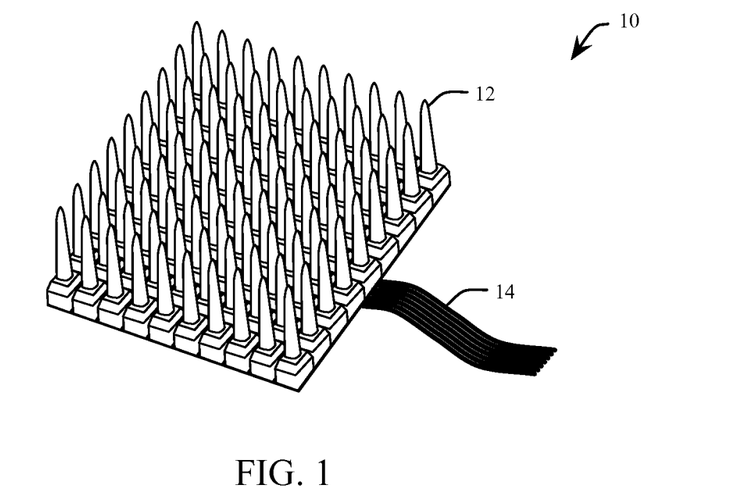
FIG. 1 is a perspective view of an intracranial BCI sensor.

FIG. 1 shows an intracortical, spike-based Brain-Computer Interface (BCI) sensor 10 used to sense biosignals. The BCI sensor 10 includes an array of electrodes 12, each of which contact at least one neuron, with each electrode having one dedicated channel by which it sends information to the BCI hardware and software. In one embodiment, the BCI sensor 10 is a 96-channel silicon microelectrode array, with a connector 14. In one example, the signals sensed by the BCI sensor 10 are filtered with an analog 4th order Butterworth with corners at 0.3 Hz and 7.5 Hz, and then digitized at 30 KHz by a 96-channel signal processor to isolate the signal band corresponding to neural action potentials (also called "spikes"). The total power in the spike band ("Spike Power") can be used as features for controlling the output of the BCI sensor. In other embodiments, the biosignals are sensed with using either Magnetoencephalography (MEG) or Functional Magnetic Resonance Imaging (fMRI). Other methods for sensing the biosignals are considered within the scope and spirit of this disclosure without departing from the self-calibration of biosignal-controlled systems.

In another embodiment, the BCI sensor 10 channels are further conditioned by binning each channel in 100 ms or 20 ms segments, buffered by 4 ms to reduce edge effects then non-causally band-pass filtered to extract action potentials ("spikes") using a 4th order Butterworth filter with corners at 250 Hz and 5000 Hz. The extracted signals are then compared to an amplitude threshold set between −3 and −4.5 times the standard deviation of the filtered signals on each channel to extract spike times. The resulting threshold crossings can also be used as features for controlling the output of the BCI sensor 10.

In one embodiment, the rate of threshold crossing events in each time segment is a feature that is used to decode the intended movement direction of a "user" of the disclosed methods, systems and devices including, without limitation, usage within research, commercial, industrial and home-use settings. In other embodiments, action potentials are used without binning and are either sorted or unsorted. Embodiments use one or more combinations of the threshold crossing rates of action potentials in binned time segments, the power in any of a number of frequency bands of the neuronal signals sensed by the BCI sensor 10, linearly or non-linearly processed versions of action potentials (e.g. squaring the signal or using the log of the signal plus one), or temporal profiles of the action potentials. Neural control can also occur solely or in combination with signals from the BCI sensor 10, detection of eye, head or finger movement or other physical responses where sufficient neural pathways exist (e.g. from the brain to the eye, head or finger) by using the decoding, calibration, and bias correction methods described herein. Example embodiments described herein include a user imagining a direction of a device, to provide convenient non-limiting examples that describe a variety of cognitive strategies for controlling the BCI.

Figure 2:
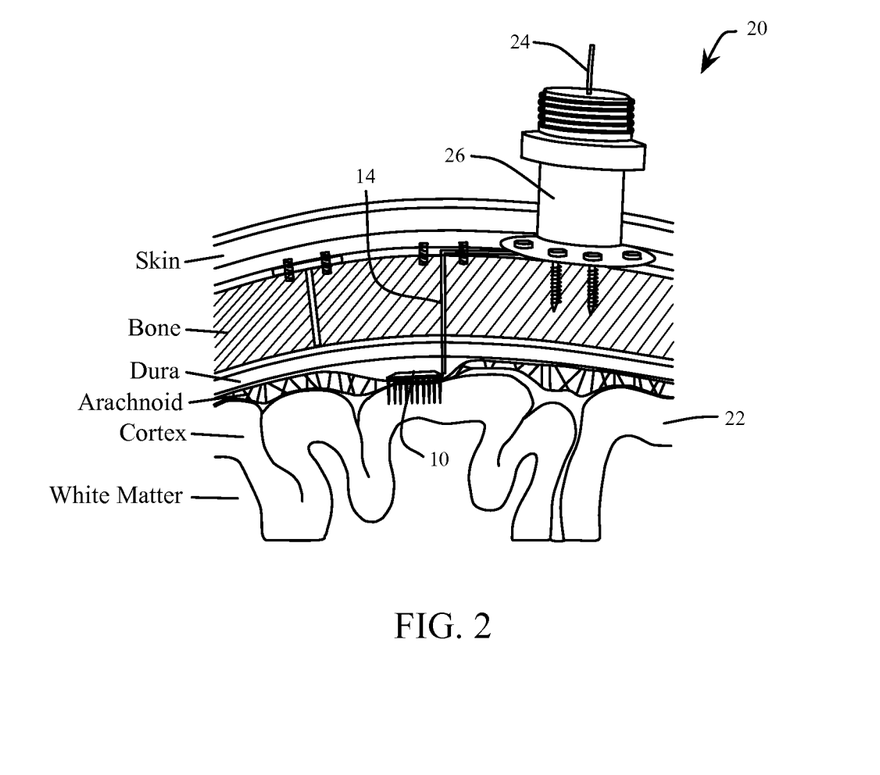
FIG. 2 is a cross-section view of a cranium illustrating the positioning of the BCI sensor of FIG. 1.

FIG. 2 illustrates the positioning of the BCI sensor 10 in a cranium of the user 20 according to one embodiment. The BCI sensor 10 is implanted so that the electrodes 12 are in contact with neurons in the cortex 22. The channels corresponding to each electrode 12 transfer electrical action potentials through the connector 14 to an output 24 in a percutaneous connector 26. In other embodiments, the BCI sensor 10 communicates through a wireless interface with a device proximally located to the user 20. Nonstationarities in these recorded biosignals cause a bias (or "offset") in the output of the effector, precluding accurate control. For example, over time the BCI sensor 10 can move within the cortex 22, thereby aligning the electrodes 12 to different combinations of neurons.

A context-aware calibration of the movement intention of the user based on measurements of neuronal signals is achieved by calibrating a decoder that correlates a plurality of neural signals to an intended movement by the user.

In one embodiment, the decoder is a Kalman filter. In other embodiments, the decoder is an optimal linear estimator, a population vector, a point process filter, a random forests decoder, or a classifier. Other decoders are envisioned within the spirit and scope of this disclosure wherein the decoders produce a control signal that is capable of deviating from the user's imagined response in some way and thus producing a bias (or offset). Non-limiting examples of the bias include a linear translation, a rotational perturbation, a shearing, a nonlinear perturbation, or any combination thereof.

A Kalman filter is a recursive Bayesian estimation algorithm that infers the desired state of an assistive device (e.g. a cursor) from the history of neural activity, (for example spike rates measured by a BCI sensor 10). The "observation model" of the filter assumes that the baseline-subtracted spike rates "z" are linearly related to the intended movement direction (e.g. imagined response) "d" at each time point "t".

$$z(t)=Hd(t)+q(t)$$

where H is the matrix relating spiking activity to the movement direction and the error term "q" is drawn from a normal distribution with zero mean and a covariance matrix "Q". The decoder's "state model" assumes that the intended movement direction at any time evolves from the movement direction in the previous time point, $$d(t)=Ad(t-1)+w(t)$$

where "A" is the matrix relating movement directions at consecutive time points and the error term "w" is drawn from a normal distribution with zero mean and covariance matrix "W". The Kalman filter is calibrated by finding the parameters H, Q, A, and W that maximize the log probability of jointly observing the set of intended movement directions D={d(1), d(2), ..., d(N)} and the set of spike rates Z={z(1), z(2), ..., z(N)}. In one embodiment, it is assumed that the neural activity at each bin reflects the users intention to move the cursor directly towards the target, without making assumptions regarding the intended cursor speed. Thus, for calibration, d(t) is set to a unit vector pointing from the location of the cursor towards the location of the target. In other embodiments, intended speed can be inferred, in which case d(t) would be scaled according to inferred speed. In one embodiment, A and W are fixed to trade-off smoothness and responsiveness of cursor movement. Accordingly, to calibrate the decoder, only the parameters H and Q are calculated to maximize the joint distribution.

In one embodiment, channels are selected for inclusion in the decoder by having a high Normalized Modulation Index (NMI), which measures the strength of the channel's directional tuning The NMI of unit "i" is defined as the norm of its Preferred Direction (PD) divided by the standard deviation of the residuals in the fit:

$$NMI=\|H_i\|/\sqrt{Q_{ii}}$$

In one embodiment, the channels are further selected based on firing rates (e.g. between 0.5 Hz and 100 Hz in one example) and signal-to-noise ratio. The aforementioned description of a decoder based on a Kalman filter is to illustrate an embodiment of the present disclosure. However, other decoders are used in alternative embodiments as described above.

In some embodiments, the use of a continuous decoder (e.g. a Kalman filter in one example) to determine the intended direction, or movement intention, of the user is complemented by a discrete decoding of a "grasp" or "click" intention to enable the user to move a cursor to an intended position and then perform a selection. The inventive concepts described herein for the continuous decoding of the neuronal signals to determine an intended direction are applicable to the discrete decoding of neuronal signals to determine a computer mouse click by the user imagining a hand grasp or similar action involving two states or positions. In one example, the hand grasp action is replaced by blinking an eye. In one embodiment, the click decoding is performed by a Linear Discriminant Analysis (LDA) classifier or some other binary classifier (such as a support vector machine, naïve bayes classifier, etc.). In another embodiment, the click decoding is performed by adding another dimension to the Kalman filter (or any continuous decoder), then performing a threshold operation to form a discrete signal corresponding to the click intention.

The inventors have realized that a combination of novel context-aware calibration methods enable autonomous control of assistive devices for clinically significant periods of time despite neural signal nonstationarities. Specifically the combination of RTI based calibration to eliminate a directional bias, an adaptive feature normalization to correct for a baseline bias, and a residual velocity bias correction provides for stable neural decoding for long periods of practical BCI use (e.g. hours or days) in self paced typing sessions performed by users with tetraplegia.

Figure 3:
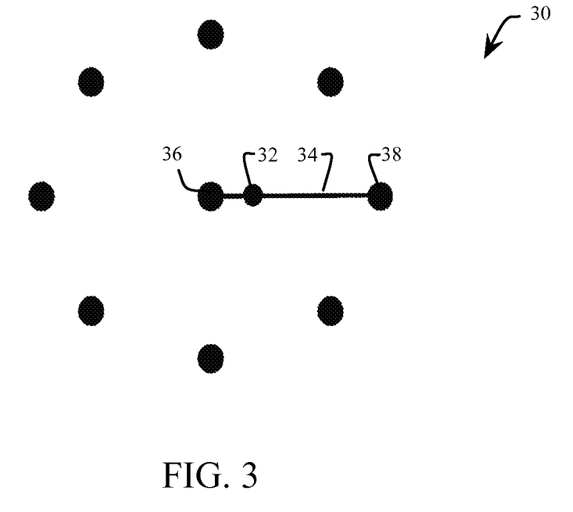
FIG. 3 is a schematic view of an open-loop center-out task.
Figure 4:
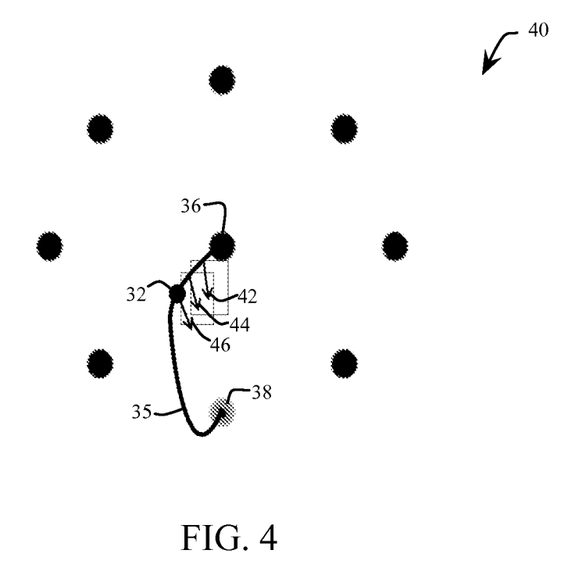
FIG. 4 is a schematic view of a closed-loop center-out task.
Figure 5:
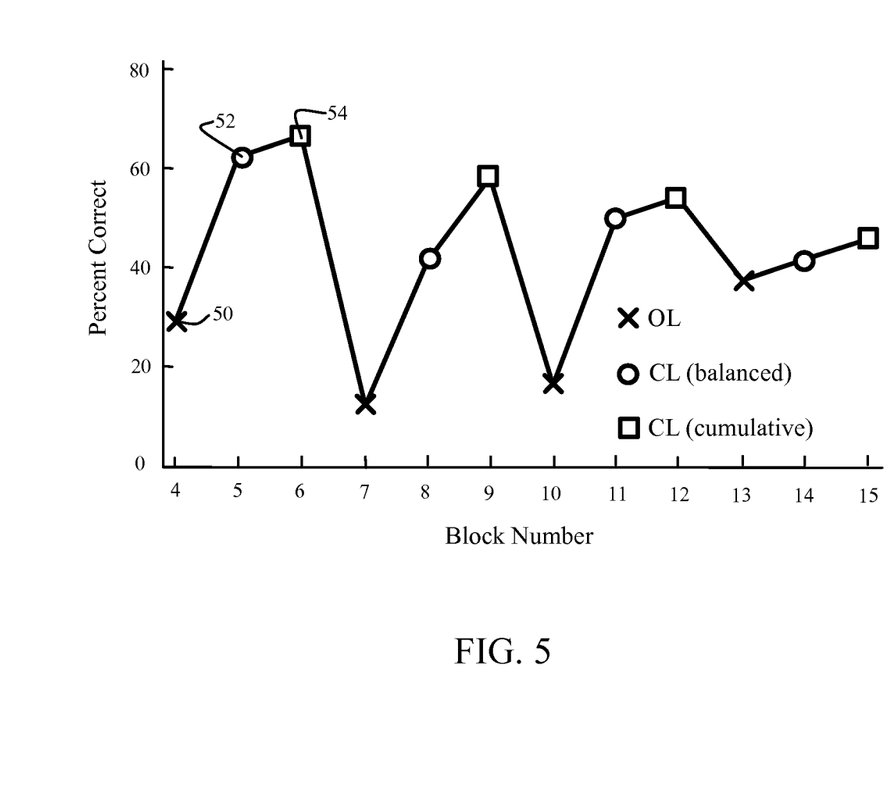
FIG. 5 is a graphical view comparing the performance of decoders calibrated using the tasks shown in FIG. 3 vs.

With reference to FIG. 3, FIG. 4 and FIG. 5, the efficacy of a standard decoder based calibration of a Kalman filter is now shown. Referring to FIG. 3 a supervised open-loop center-out (OL-CO) task 30 is performed (also referred to as supervised decoder calibration) with presented targets, designed for the purpose of calibrating a decoder. The BCI user (e.g. user) is asked to imagine controlling the computer cursor, which is actually under the control of the computer.

The user imagines moving a cursor 32 along a straight path 34 from a center 36 to one of a plurality of targets 38, while the cursor 32 is moved independent of the user's neural activity. This process is repeated for each of the targets 38 surrounding the center 36. Standard decoder based calibration is then performed based on the imagined movement and the actual movement of the cursor.

FIG. 4 shows a supervised closed-loop center-out (CL-CO) task 40. The CL-CO task is the "closed-loop" version of the task shown in FIG. 3; called closed-loop because the cursor's movement is under neural control. The CL-CO task 40 is performed by moving the cursor 32, (which due to errors follows the trajectory 35), from the center 36 to one of a plurality of targets 38. In contrast to the OL-CO task 30 of FIG. 3, the CL-CO task 40 uses the user's decoded neural activity to directly control the continuous movement of the cursor in real time along the trajectory 35. At various points along the trajectory 35, because of noise and nonstationarity, the decoded movement will differ from the ideal direction, but the intended movement can be inferred to have been directly toward the target at each moment along that trajectory, as shown by directional vectors 42, 44 and 46. Similar to the OL-CO task 30, standard decoder based calibration is then performed by regressing the imagined movement at each time segment along the trajectory 35 with the recorded neural activity.

FIG. 5 illustrates that for a number of test sessions (activity blocks), the decoder calibration provides a higher percentage of correct movements (e.g. the intended movement and actual movement are closely matched along a trajectory), when using the CL-CO method 52 rather than the OL-CO method 50. Furthermore, the cumulative use 54 of the CL-CO method 52 yields an even higher percentage of correct movements compared to the single use of the CL-CO method 52. The improved performance of the CL-CO method 52 over the OL-CO method 50 is due, in part, to the context dependence of neural tuning (e.g. neuronal activity will be more representative of intended cursor movement when the user actually controls the cursor movement). Another reason for the improved performance is increased mental engagement in a closed-loop task than an open-loop task (in the latter, the cursor would move the same way whether or not the person was attending to the task). A final reason for the improved performance in the CL cumulative blocks is the increased amount of data used for decoder calibration. The latter two advantages also extend to RTI decoder calibration.

Figure 6:
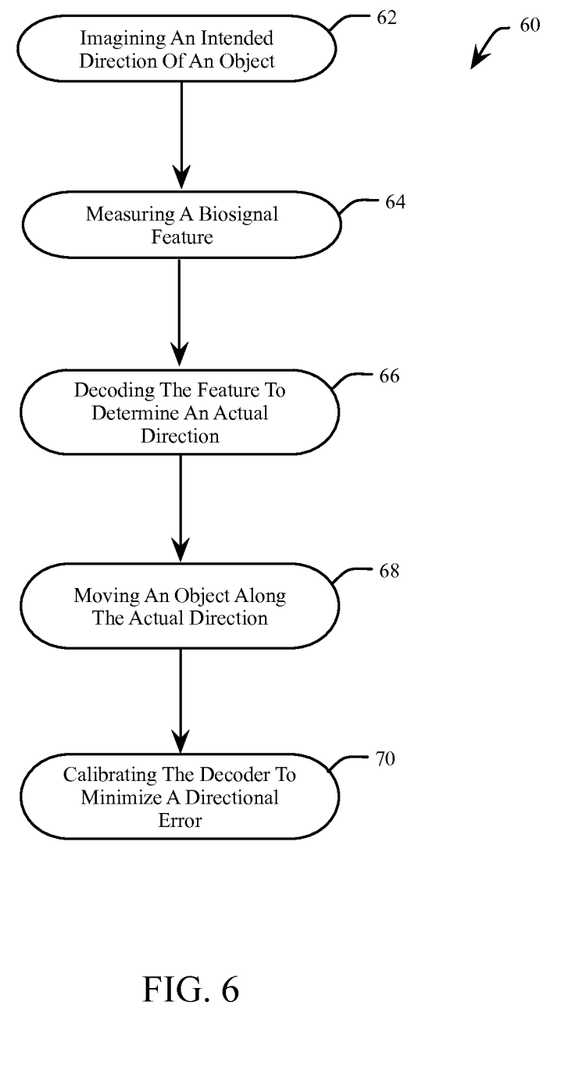
FIG. 6 is a flowchart representation of a method for decoder calibration using Retrospective Target Inference (RTI).

FIG. 6 shows the steps for an RTI based calibration 60 in accordance with an embodiment of the present disclosure. RTI based calibration 60 is an advancement over traditional closed-loop calibration that allows the decoder to be recalibrated using data acquired during practical BCI use, in which the user chooses their own targets out of a potentially infinite array of possibilities. The target that the user ultimately selects is retrospectively inferred to be towards the direction that the user was aiming during the preceding time bin. With reference to FIG. 6, at step 62, a user imagines an intended direction of an object (e.g. a cursor) towards a letter on a keyboard, for example. Imagining is a non-transitory electrochemical process of the brain, wherein neurons produce changes in their signals, which can be measured by electrical action potentials or other neural features, as described above. The neural signals are one instantiation of biological signals (biosignals) that are measured at step 64. For example, the biosignals are neuronal signals measured by the BCI sensor 10. In another example, the biosignals can be eye or head movements resulting from neuronal signals communicating with the eye or head respectively. At step 66, one or more features (e.g. threshold crossing rate in one example) are decoded to determine an actual direction based on the previous calibration of the decoder. At step 68, an object (e.g. a cursor 32) is moved along the actual trajectory 35 using the decoded biosignals. At step 70, the decoder is calibrated to minimize a directional error using the recorded neural signals and the retrospectively inferred target direction. Specifically, the unit vectors corresponding to the intended direction (e.g. of the cursor) are regressed against the corresponding neural activity to obtain the Kalman filter coefficients H and Q.

When using threshold crossing counts as the feature for decoding, neurons can appear and disappear over time on a given channel, which can lead to changes in tuning on that channel. Decoder angular and torsional bias (e.g. directional bias) caused by changes in the tuning of the decoded biosignals is reduced by retrospectively inferring the user's intended movement direction at each moment based on the location of the next selection, and using the method shown in FIG. 6.

During practical BCI use, the user might spend time between target selections with no particular movement intention or goal. In the case of typing, it might take time for the user to decide on the next word to type, search for the next letter, or check the word completion/prediction list for the desired word. Thus, for RTI based decoder calibration, it is particularly important to ensure that only data related to movement intention are included in the calibration data.

In one instantiation, the time periods used for calibration are selected using a simple set of heuristics: include time bins in which the cursor moved closer to the next selected target, discard periods immediately preceding a neural click, and discard periods that occurred long before a selection (to allow the user to take as much time as needed to decide on the next selection). In one example, a period of five seconds was used prior to the selection, after discarding the time period just before the click. Data immediately preceding the neural click is discarded because the neural activity is influenced by the user preparing to generate the neural click, and because the angular estimate of the user's intended movement direction is less accurate when the cursor is closer to the target. In one example, data points that occurred within 300 ms of target selection and data points wherein the cursor was within 1.5 cm of the next selected target were excluded from decoder calibration.

Although RTI based decoder calibration reduces nonstationarities in angular tuning, nonstationarities can also develop in baseline threshold crossing rates resulting in a directional bias in cursor motion from sources unrelated to the intention to direct the cursor.

In one example of autonomous use of an assistive device not involving a self-paced session, feature means are updated in batch by using the raw average of the neuronal firing rates from the most recent activity block that was included in each decoder calibration, or from a baseline of the cosine tuning function fit to each neural feature. During real-time decoding, these estimated baseline rates were subtracted from each feature before decoding.

Firing rates of single and multiunit activity can change on the timescale of minutes to hours because of physiological and/or recording nonstationarities. Because mean rates can change between blocks of neural control (e.g. during rest periods), the estimate of the mean rates is also updated during rest periods with adaptive feature normalization. This allows each block to begin with a more accurate estimate of the features' means, by subtracting the baseline rate for each channel before sending each channels ongoing neural data to the decoder. In one example, the rest period is a user-timed break in BCI use.

In another example, involving autonomous use of an assistive device with a self-paced session, the intervals of time between recording activity blocks are arbitrarily long, thus leading to large nonstationarities. The estimate of baseline rates is iteratively updated between blocks of neural control, during the rest periods, using an exponentially weighted running mean and variance. Specifically, the mean and variance of each feature (e.g. threshold crossing rate, spike power, etc.) are computed in real time using a recursively-defined exponential estimate of each with a time constant (e.g. 120 or 240 sec in two examples) as follows:

$$\mu_t = \{(\tau-1)/\tau\} * \mu_{t-1} + (z_t/\tau)$$

$$\sigma_t^2 = \{(\tau-1)/\tau\} * \sigma_{t-1}^2 + (z_t - \mu_{t-1})^2/\tau$$

where $\mu_t$ is the current estimate of the mean for a given feature, $\sigma_t$ is the standard deviation (SD) and $\sigma_t^2$ is the variance, $z_t$ is the current sample value, and $\tau$ is the time constant.

In another embodiment of a self-paced session, a heuristic is added to allow features to adapt quickly to large, discrete baseline shift events. Specifically, if the current sample exceeds the estimated mean by more than ten times the estimated SD, the mean and SD-tracking is performed with a fast-adapting phase as follows:

$$\mu_t = \{(t-t_0-1)/(t-t_0)\} * \mu_{t-1} + z_t/(t-t_0)$$

$$\sigma_t^2 = \{(t-t_0-1)/(t-t_0)\} * \sigma_{t-1}^2 + (z_t - \mu_{t-1})^2/(t-t_0)$$

where $t_0$ is the time at which the feature exceeds this threshold. The effect of this heuristic is to quickly adapt the estimate of the mean and variance with any large noise event, and then to equally, (rather than exponentially), weight all time points from $t_0$ until $t-t_0=\tau$ then resume the recursive feature tracking without the aforementioned heuristic. Subsequently, the mean is subtracted and the SD divided from each feature to maintain a zero-mean and unit-SD feature input to the decoder. In one embodiment, a small offset is added to the SD to prevent a division by zero. In another embodiment, the aforementioned exponential estimate is replaced with a batch estimate, a smoothly varying boxcar filter or a sudden reset in response to an abrupt change in the mean or variance.

With reference to FIG. 7 through FIG. 10, the method of velocity bias correction will be explained. Because mean rates can also change during blocks of neural control, we must use a method to mitigate bias during blocks of neural control. Adaptive feature normalization doesn't work as well as during blocks, because if a bias develops, periods of time during which the user is trying to fight the bias are used when computing the new mean estimate for each cell, which makes the bias worse. Specifically, if the time constant of mean estimation is short, mean subtraction will dampen the effects of actual neural modulation related to voluntary movement intent, and cause a subsequent bias opposite to the intended movement. If the time constant is sufficiently long to not cause a bias, then mean subtraction takes longer to counter biases resulting from actual signal nonstationarities. As soon as a bias appears, the user would then have to counteract the bias by modulating their neural activity, but then the neural activity resulting from counteracting the bias would enter into the estimation of the new mean rates. Thus, in either situation, where the time constant is either too short or too long, the bias would effectively never disappear.

Instead, to mitigate the effect of nonstationarities during neural control, the velocity bias is iteratively estimated so that only high-speed decoded movements are used to update the estimate of the bias direction. This velocity bias is then subtracted from the subsequently decoded movements of the assistive device (e.g. cursor). In one embodiment, the high-speed decoded movements are determined by using a threshold, below which the movements are discarded. In another embodiment, the high-speed movements are proportionally weighted to provide a greater contribution to reducing the velocity bias than relatively lower speed movements.

This method iteratively estimates the direction and magnitude of bias, and then feeds it back and subtracts it from the commanded output. The bias is estimated using a running average of only the outputs that exceed a given threshold outside of normal operating range, which is prescribed by the context of the effector. In one example, the threshold is the $66^{th}$ percentile of the decoded speeds estimated during the most recent filter calibration, although other percentiles are used depending on the context of the effector.

In another embodiment, new samples are added to the estimate only when a speed threshold is exceeded, and are weighted using an exponential decay function to yield an estimated bias to subtract from the commanded velocity in future time-steps.

Figure 7:
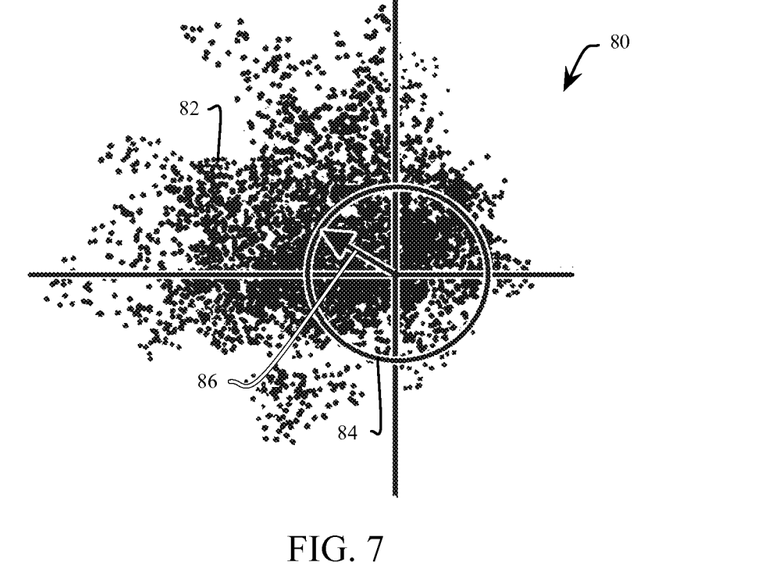
FIG. 7 is a graphical view of decoded velocities with an estimated mean bias.
Figure 8:
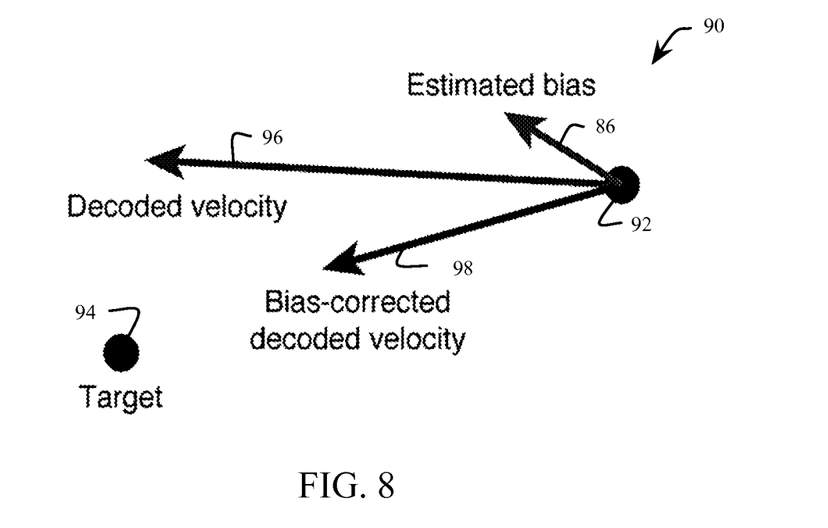
FIG. 8 is a graphical view showing application of the mean bias of FIG. 7 to correct a decoded velocity bias.

FIG. 7 is a graphical view showing a method of velocity bias correction 80. The plurality of decoded velocities 82 that exceed a threshold 84 are used to determine a direction and magnitude of an estimated bias 86. In FIG. 8 the user imagines a movement of a cursor 92 towards a target 94 by generating neuronal activity, which is decoded to produce an imagined velocity 96 (e.g. the direction and magnitude of the intended direction). The estimated bias 86 is subtracted from the imagined velocity 96 to produce a bias-corrected decoded velocity 98.

Figure 9:
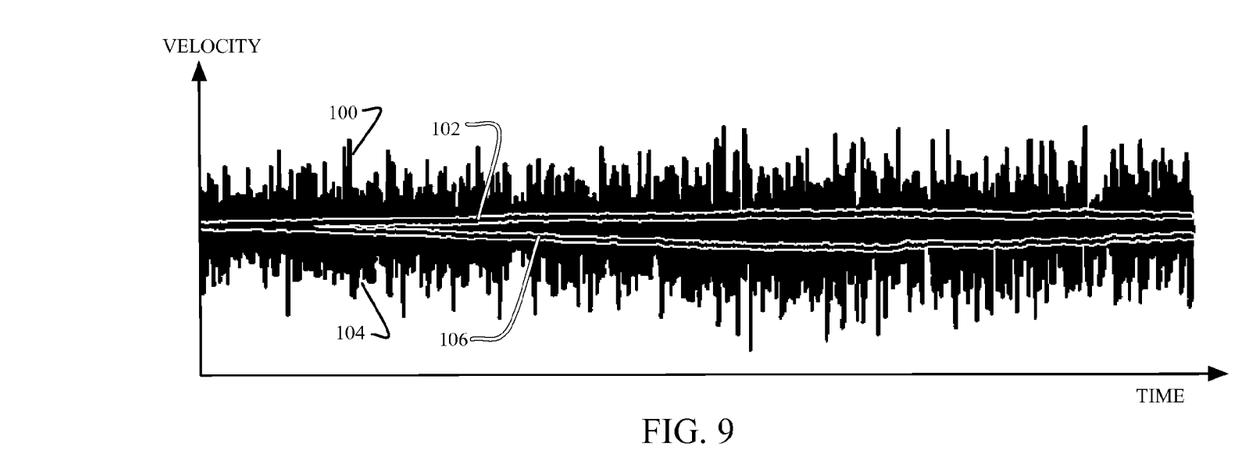
FIG. 9 is a graphical view of decoded velocities in x and y from a block of neurally controlled point-and-click typing without velocity bias correction.
Figure 10:
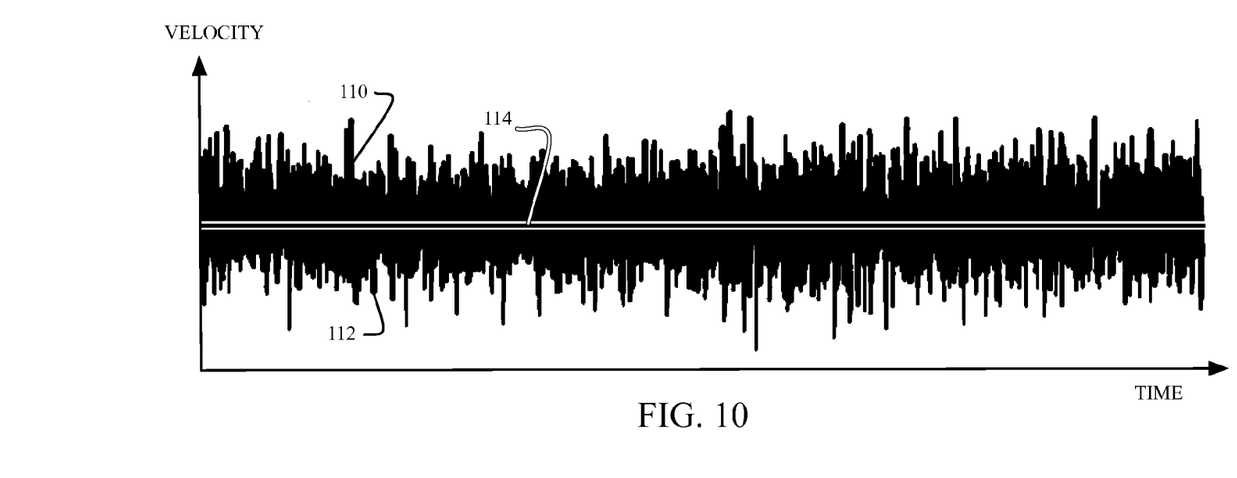
FIG. 10 is a graphical view of decoded velocities in x and y from the same block of neurally-controlled typing in FIG. 9, but with correction for velocity bias.

With reference to FIG. 9, a series of decoded velocities 100 (and 104) with a mean velocity in x 102 and y 106 demonstrates biases due to nonstationarities in the decoded velocities. FIG. 10 shows the same series of decoded velocities 110 and 112 with a mean velocity in both x and y 114 near [0 0] after estimation and correction of the velocity bias.

Figure 11:
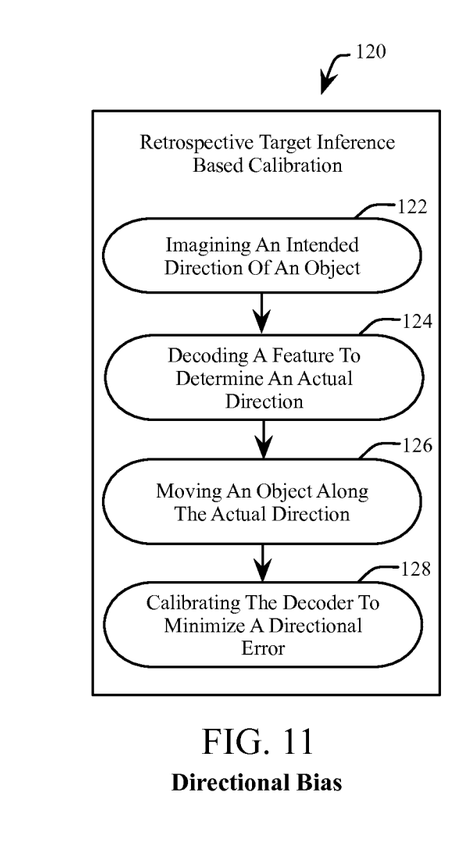
FIG. 11 is a flowchart representation of a method for decoder calibration to remove or reduce angular or torsional bias using RTI.
Figure 12:
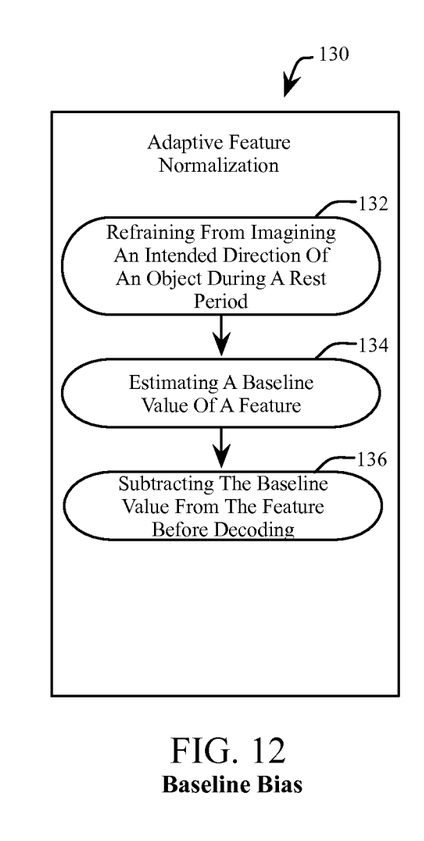
FIG. 12 is a flowchart representation of a method for correction of a baseline bias in the features used for decoding.
Figure 13:
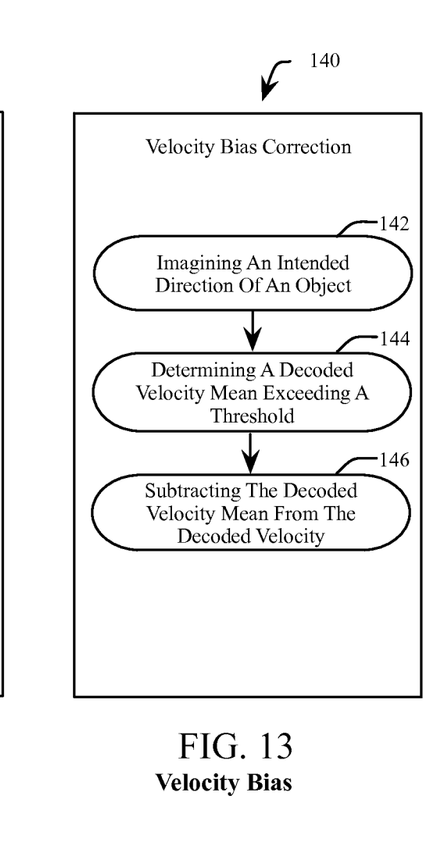
FIG. 13 is a flowchart representation of a method for correction of any residual velocity bias, after the corrections in FIGS. 11 and 12 are applied.

In accordance with one embodiment of the present disclosure, FIG. 11, FIG. 12 and FIG. 13 show the combined approach of using RTI based calibration 120 to correct for directional bias (e.g. to remove or reduce angular or torsional bias), using adaptive feature normalization 130 to correct for baseline bias in features used for decoding, and using velocity bias correction 140 to correct for any residual velocity bias after the corrections of the methods shown in FIG. 11 and FIG. 12 are applied. The combination of these methods provide for stable neural decoding for long periods of autonomous control of assistive devices.

With reference to FIG. 11 at step 122, the user imagines an intended direction of an object. At step 124, a feature is decoded to determine an actual direction. At step 126, an object is moved along the actual direction. At step 128, the decoder is calibrated to minimize a directional error between the intended direction and the actual direction.

With reference to FIG. 12, at step 132, the user refrains from imagining an intended direction of an object during a rest period. At step 134, a baseline value of a feature is estimated. At step 136, the baseline value is subtracted from the feature before decoding.

With reference to FIG. 13, at step 142, the user imagines an intended direction of an object. At step 144, a decoded velocity mean that exceeds a threshold is determined. At step 146, the decoded velocity mean is subtracted from the decoded velocity.

Figure 14:
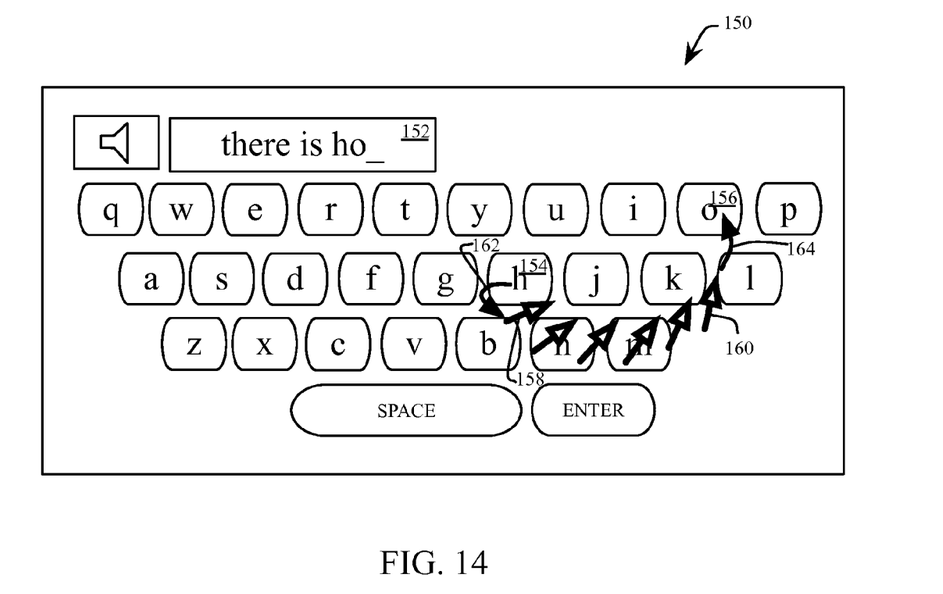
FIG. 14 is a schematic view of a virtual QWERTY keyboard illustrating inferred intended directions used for RTI decoder calibration.
Figure 15:
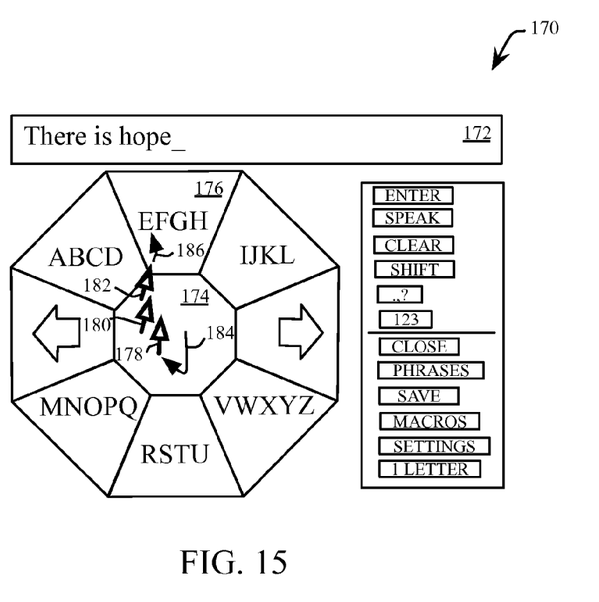
FIG. 15 is a schematic view of a radial keyboard illustrating inferred intended directions used for RTI decoder calibration.
Figure 16:
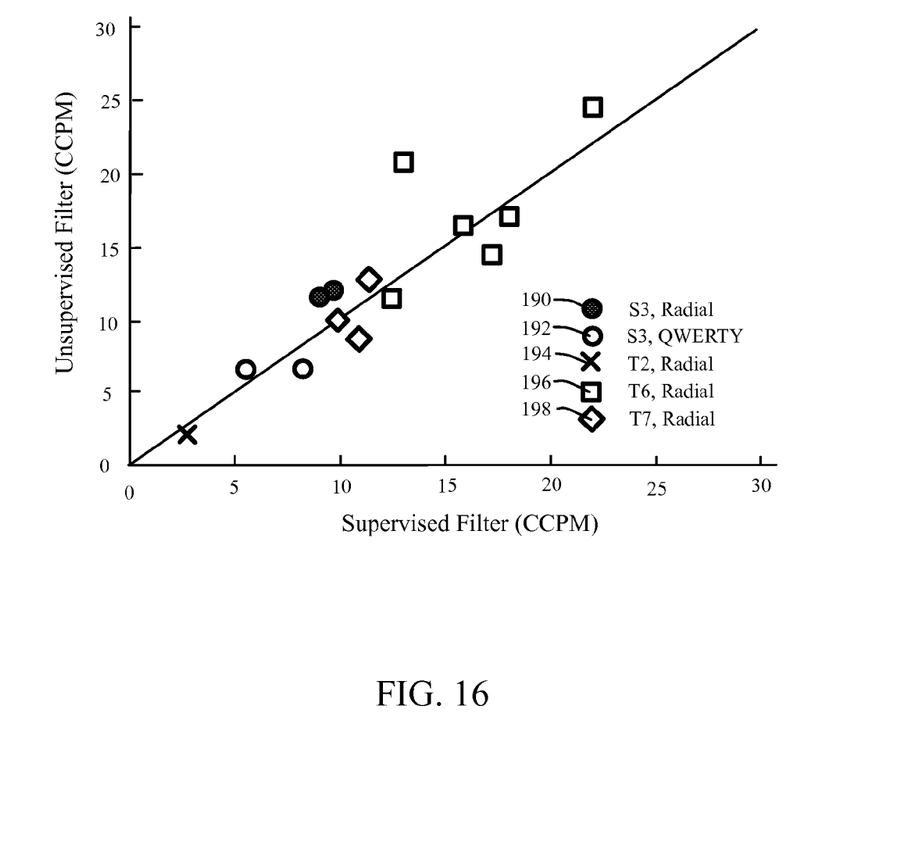
FIG. 16 is a graphical view comparing the efficacy of traditional and RTI decoder calibration.

With reference to FIG. 14, FIG. 15 and FIG. 16, the combined application of the calibration methods of FIG. 11, FIG. 12 and FIG. 13 is shown to successfully enable autonomous control of assistive devices. With reference to FIG. 14, the user imagines a movement of a cursor on a QWERTY keyboard 150 to produce a sentence on a display 152. The user moves a cursor from the previous letter 154 to the next letter 156 by a series of intended trajectories beginning with a first direction 158 and ending with a last direction 160. An initial intended direction 162, preceding the first direction 158 is discarded for the purposes of decoder calibration as previously described for the method of RTI based calibration. Similarly, the final segment of the intended direction 164 is discarded from directional decoder calibration.

With reference to FIG. 15, the user imagines a movement of a cursor on a radial keyboard 170 to produce a sentence on a display 172. The user moves a cursor from a previous position 174 to a letter selection 176, through a series of intended trajectories 178, 180 and 182. An initial intended direction 184, preceding the first direction 178 is discarded for the purposes of decoder calibration as previously described for the method of RTI based calibration. Similarly, the final segment of the intended direction 186 is discarded for the purposes of decoder calibration.

Referring to FIG. 16, the results of five tests 190, 192, 194, 196 and 198 using a combination of QWERTY and radial keyboards, shows excellent correlation of typed Correct Characters Per Minute (CCPM) between the use of the combined methods of FIG. 11, FIG. 12 and FIG. 13 (e.g. "unsupervised filter", "traditional" or "standard decoder") and a supervised filter (e.g. RTI).

Figure 17:
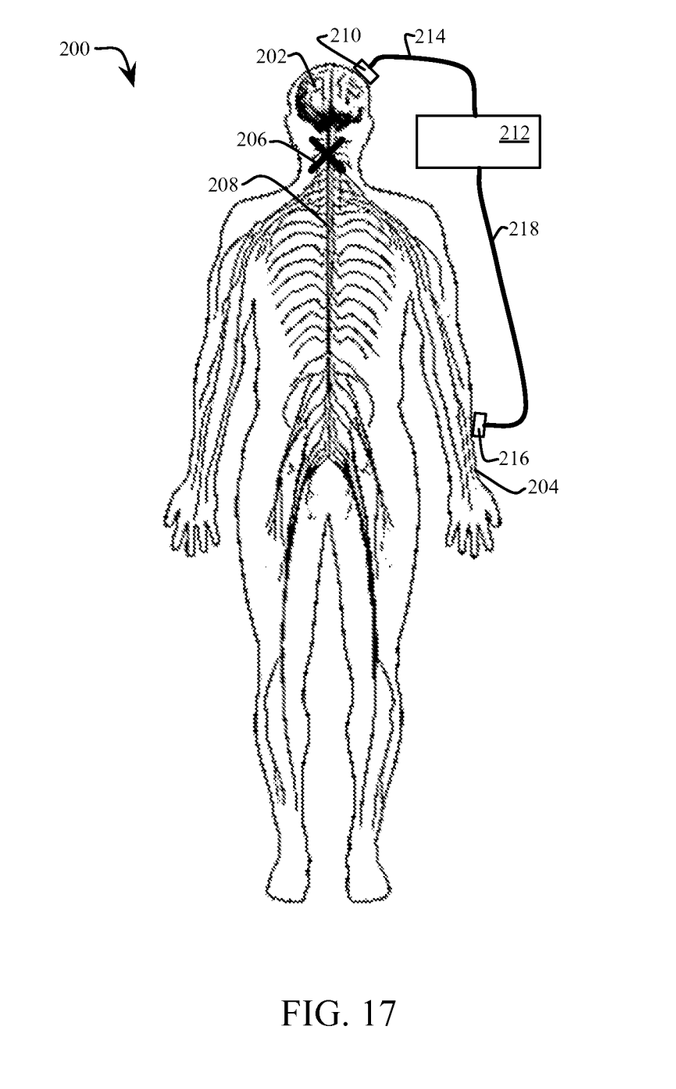
FIG. 17 is a schematic view of a system for autonomous control of an assistive device.

FIG. 17 shows a system 200 for autonomous control of an assistive device 204 (e.g. a prosthetic limb). A brain 202 of a user has an impediment 206 to a neural pathway 208 (e.g. a spinal injury disconnecting the brain from a limb), thereby electrically decoupling the brain 202 from the assistive device 204. A biosensor 210 (e.g. BCI sensor) receives neuronal signals from the brain 202 and transmits these signals to a controller 212 through a first connector 214. In one example, the controller 212 includes a Kalman filter and devices configured to calibrate the filter and correct for output biases according the methods shown in FIG. 11, FIG. 12 and FIG. 13. The controller controls a transducer 216 through a second connector 218. The transducer 216 is configured to move the assistive device 204 along an intended direction.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements.

What is claimed is:

1. A method for context-aware self-calibration comprising:
    measuring for a plurality of time segments, at least one feature of at least one biosignal for each of at least one channel, each biosignal created in response to a user imagining an intended direction for each time segment;
    moving an object along an actual decoded direction determined by an output of a decoder configured to correlate for each time segment the at least one feature to the intended direction;
    calibrating the decoder to minimize, for each time segment, an error between the actual decoded direction, and the intended direction inferred subsequent to the respective time segment; and
    normalizing each feature during a rest period, including refraining by the user from imagining the intended direction for at least one time segment, and estimating a baseline value of each feature with a recursively-defined exponential estimate, the baseline value of each feature being subtracted from each respective feature for each time segment before being decoded by the decoder.

2. The method of claim 1 wherein a set of time segments is chosen from the plurality of time segments occurring within a first time of the user imagining the intended direction, prior to at least one of a second time at the end of the actual decoded direction and reaching a proximal distance at the end of the actual decoded direction.

3. The method of claim 1 wherein the set of time segments includes the at least one channel with a signal to noise ratio (SNR) exceeding an SNR threshold.

4. The method of claim 1 wherein calibrating the decoder includes exponentially reducing a contribution of the error for each time segment to calibrating the decoder, in proportion to a temporal proximity of each time segment to a current time segment.

5. The method of claim 1 wherein calibrating the decoder includes scaling the error for a recent set of time segments when a range of errors for each time bin exceeds a stability threshold.

6. The method of claim 1 wherein the plurality of time segments are from one of a plurality of activity blocks, and the user imagines the intended direction towards a target for the respective activity block.

7. The method of claim 1 wherein the biosignal is created by at least one neuron of the user, and the at least one feature includes a threshold crossing rate of the at least one biosignal.

8. The method of claim 1 wherein the biosignal is responsive to a movement of an eye of the user, and includes at least one of an electrical signal and an optical signal.

9. The method of claim 1 wherein the biosignal is responsive to a movement of a head of the user, and includes at least one of an electrical signal and an optical signal.

10. A method for autonomous control of assistive devices comprising:
measuring for a plurality of time segments, at least one feature of at least one neuronal signal for each of a plurality of channels, each channel associated with at least one neuron of a user, each neuronal signal created by the at least one neuron;
decoding the at least one neuronal signal to move an object along an actual decoded direction determined by an output of the decoder configured to correlate for each time segment, wherein the user imagines an intended direction, the at least one feature to the intended direction;
calibrating the decoder by minimizing an error between the actual decoded direction, and the intended direction inferred subsequent to the respective time segment;
normalizing the at least one feature during a rest period, wherein the user refrains from imagining the intended direction, by estimating a baseline value of each feature with a recursively-defined exponential estimate, the baseline value of each feature being subtracted from each respective feature for each time segment before being decoded by the decoder; and
correcting a velocity bias, wherein the user imagines the intended direction, by determining an exponentially weighted running mean of a decoded velocity for each respective time segment exceeding a speed threshold, and subtracting the exponentially weighted running mean from the decoded velocity.

11. The method of claim 10 wherein the decoder is a Kalman filter.

12. The method of claim 10 wherein the feature is a threshold crossing rate of the at least one action potential.

13. The method of claim 10 wherein the feature is an RMS power of the at least one action potential.

14. The method of claim 10 wherein the velocity threshold is a predetermined centile of a decoded velocity of a most recent decoder calibration.

15. A system for autonomous control of assistive devices comprising:
a user imagining an intended direction for each of a plurality of time segments by generating at least one biosignal from a part of the user;
a biosignal sensor configured to measure for the plurality of time segments, at least one feature of the at least one biosignal for at least one channel;
a device electrically decoupled from the part of the user;
a decoder configured to correlate for each time segment, the at least one feature to the intended direction, wherein an object is moved along an actual decoded direction determined by an output of the decoder, and the decoder is calibrated by minimizing an error between the actual decoded direction, and the intended direction inferred subsequent to the respective time segment; and
wherein each feature is normalized during a rest period, including refraining by the user from imagining the intended direction for at least one time segment, and a baseline value of each feature is estimated with a recursively-defined exponential estimate, the baseline value of each feature being subtracted from each respective feature for each time segment before being decoded by the decoder.

16. The system of claim 15 wherein a velocity bias is corrected while the user is imagining the intended direction by determining an exponentially weighted running mean of a decoded velocity for each respective time segment exceeding a speed threshold, and subtracting the exponentially weighted running mean from the decoded velocity.

17. The system of claim 15 wherein the device is a prosthetic limb mechanically coupled to the user.

18. The system of claim 15 wherein the device is a robotic arm mechanically decoupled from the user.

19. The system of claim 15 wherein the device is a cursor.

20. A method for context-aware self-calibration comprising:
measuring for a plurality of time segments, at least one feature of at least one biosignal, each biosignal created in response to an intended action for each time segment;
performing an actual action determined by an output of a decoder configured to correlate for each time segment the at least one feature to the intended action;
calibrating the decoder to minimize, for each time segment, an error between the actual action, and the intended action inferred subsequent to the respective time segment; and
normalizing each feature during a rest period, including refraining by a user from imagining the intended action for at least one time segment, and estimating a baseline value of each feature with a recursively-defined exponential estimate, the baseline value of each feature being subtracted from each respective feature for each time segment before being decoded by the decoder, and wherein the user generates each biosignal.

* * * * *